United States Patent [19]
Arkell et al.

[11] 3,959,381
[45] May 25, 1976

[54] PHENOL AND CYCLOHEXANONE MANUFACTURE

[75] Inventors: Alfred Arkell, Wappingers Falls, N.Y.; Peter A. Riedl, Vienna, Austria; Edwin R. Kerr, Wappingers Falls, N.Y.

[73] Assignee: Texaco Inc., New York, N.Y.

[22] Filed: Oct. 22, 1970

[21] Appl. No.: 83,158

[52] U.S. Cl. ............... 260/586 R; 260/610 B; 260/621 C
[51] Int. Cl.² ............. C07C 45/00; C07C 37/08; C07C 179/02
[58] Field of Search ......... 260/586 R, 621 C, 610 B

[56] References Cited
UNITED STATES PATENTS

| | | | |
|---|---|---|---|
| 2,628,984 | 2/1953 | Aller et al. | 260/621 C |
| 2,744,143 | 5/1956 | Filar | 260/621 C |
| 2,748,165 | 5/1956 | Kroeper et al. | 260/621 C X |
| 2,889,368 | 6/1959 | Hiratsuka et al. | 260/621 C X |
| 2,950,320 | 8/1960 | Vandenburg | 260/621 C X |
| 2,993,074 | 7/1961 | Shepard | 260/621 C X |

*Primary Examiner*—Norman Morganstern
*Attorney, Agent, or Firm*—T. H. Whaley; C. G. Ries; Robert A. Kulason

[57] ABSTRACT

Method of producing phenol and cyclohexanone in enhanced yields consisting essentially of contacting cyclohexylbenzene, preferably in the presence of a member selected from the group consisting of cumene and cumene hydroperoxide, with an oxygen containing gas to form 1-phenylcyclohexyl hydroperoxide containing intermediate product, optionally purifying said intermediate, contacting the 1-phenylcyclohexyl hydroperoxide intermediate product with an acid cleavage catalyst in the presence of an alkanone of from 3 to 6 carbons and recovering the formed phenol and cyclohexanone.

2 Claims, No Drawings

PHENOL AND CYCLOHEXANONE MANUFACTURE

BACKGROUND OF INVENTION

In the past, one method for manufacturing phenol and cyclohexanone called first for the hydroalkylation of benzene to form cyclohexylbenzene, the cyclohexylbenzene in turn being oxidized to phenylcyclohexyl hydroperoxide, the phenylcyclohexyl hydroperoxide then being subjected to acid catalyzed cleavage to form phenol and cyclohexanone. Although this prior method produced phenol and cyclohexanone in reasonably adequate quantities, there is a continuous search for improvement in yields and selectivity therein.

SUMMARY OF INVENTION

We have discovered and this constitutes our invention a method of producing phenol and cyclohexanone products from cyclohexylbenzene in improved yields and selectivity. More specifically, the invention comprises contacting cyclohexylbenzene, preferably in the presence of a member selected from the group consisting of cumene and cumene hydroperoxide, with an oxygen containing gas to form 1-phenylcyclohexyl hydroperoxide and cumyl hydroperoxide (if said member is employed) and contacting the resultant hydroperoxide intermediate product with an acid cleavage catalyst in combination with an alkanone of from 3 to 6 carbons. Unreacted cumene is preferably removed from the intermediate product prior to cleavage.

DETAILED DESCRIPTION OF THE INVENTION

In detail, the method of the invention is a two-stage procedure. In the first stage cyclohexylbenzene is contacted with an oxygen containing gas at a temperature between about 90° and 140°C. utilizing a mole ratio of oxygen to cyclohexylbenzene of at least about 3:1 and up to 100:1 or more to form a crude 1-phenylcyclohexyl hydroperoxide. Under preferred conditions, a member selected from the group consisting of cumene or cumene hydroperoxide is also employed in the first stage reaction in an initial mole ratio of cyclohexylbenzene to said member of between about 1:99 and 99:1, preferably between about 1:3 and 3:1. The cumene hydroperoxide, when employed, is either initially introduced or formed in situ. It functions to suppress the formation of undesired hydroperoxide by-products such as 5-benzoyl-1-pentyl hydroperoxide and thereby enhances the yield of 1-phenylcyclohexyl hydroperoxide intermediate. The increased intermediate yield in turn contributes to the higher phenol and cyclohexanone final product yield. Of equal importance, the decreased formation of impurity hydroperoxide decreases the production of aldehydes during the subsequently described second stage thereby increasing the recovery of cyclohexanone final product which would otherwise react with the aldehydes.

The crude 1-phenylcyclohexyl hydroperoxide containing product is desirably purified before introduction into the second stage. Purification is accomplished by means such as removing unreacted cumene (if employed) and at least a portion of the cyclohexylbenzene, e.g., at between about ambient and 90°C. under between about 0.1 and 0.5 mm Hg pressure. This removal decreases or eliminates compounds containing tertiary benzylic hydrogens thereby aiding in the enhancement of a phenol and cyclohexanone acid cleavage yields. When cumene and cumene hydroperoxide are not employed in the first stage, it is also advantageous to engage in an additional purification step, i.e., treating the distillation residue, e.g., with a lower liquid alkane, e.g., 5 to 10 carbons, to separate the 1-phenylcyclohexyl hydroperoxide as extract from the impurity hydroperoxide by-products. This second purification is normally not necessary when cumene and cumene hydroperoxide are employed in the first stage since the cumyl member functions to materially suppress oxidation by-product formation. When extraction is employed, it is normally conducted between about 0° and 50°C. using between about 5 and 10 volumes liquid alkane/volume distillation residue.

In the second stage of the reaction the purified or unpurified 1-phenylcyclohexyl hydroperoxide containing intermediate product is then contacted with an acid cleavage catalyst selected from the group consisting of organic sulfonic acids and mineral acids in the presence of an alkanone of 3 to 6 carbons at a temperature between about ambient (~20°C.) and 50°C. wherein said catalyst concentration is between about 10 and 30 wt. % based on the reaction mixture and said alkanone concentration is between about 20 and 80 wt. % based on said mixture. The alkanone has been found to enhance phenol and cyclohexanone yields by reacting with aldehyde by-products which are formed during the acid catalyzed cleavage of the impurity hydroperoxides such as 5-benzoyl-1-pentyl hydroperoxide carried over from the first stage. The aldehyde by-products are undesirable since under acid cleavage conditions they consume the desired phenol and cyclohexanone products through condensation. Impurity hydroperoxide by-products such as 5-benzoyl-1-pentyl hydroperoxide are formed during the thermal degradation of 1-phenyl cyclohexyl hydroperoxide under oxidizing conditions.

Under preferred conditions, both the first and the second stages are subjected to agitation, e.g., stirring in order to facilitate reactant contact.

Specific examples of oxygen containing gas contemplated herein are oxygen, air and synthetic gaseous mixtures of oxygen with inert gas such as oxygen-nitrogen mixtures wherein oxygen content is between about 30 and 90 volume %.

Specific examples of alkanones contemplated herein are acetone, methylethyl ketone, ethylethyl ketone and ethylpropyl ketone.

Specific examples of the acid cleavage catalysts contemplated herein are $H_2SO_4$, HCl, $H_3PO_4$, $HNO_3$, $H_2SO_3$, methane sulfonic acid, ethane sulfonic acid, propane sulfonic acid, p-toluene sulfonic acid, benzene sulfonic acid, sulfonated polystyrene (Amberlyst 15 - Rohm and Haas).

Examples of the liquid alkane extractants suitable in the optional purification are pentane, hexane and octane.

The following examples further illustrate the method of the invention but are not to be construed as limitations thereof.

EXAMPLE I

This example illustrates the method of the invention in the absence of cumene and cumene hydroperoxide and emphasizes the desirability of purifying the 1-phenylcyclohexyl hydroperoxide intermediate.

FIRST STAGE

To a 1-liter glass reactor equipped with a reflux condenser, gas sparger and mechanical stirrer, 250 grams of cyclohexylbenzene were charged. The temperature was maintained at 120°C. by means of an oil bath. Oxygen was sparged into the reactor at a low rate of 0.2 liter/minute. After 670 minutes 20.2 mole % of cyclohexylbenzene had been converted to 1-phenylcyclohexyl hydroperoxide with a selectivity of 79.5 mole %.

SECOND STAGE

To a 0.1 liter flask fitted with a mechanical stirring device and reflux condenser in two separate runs there was respectively charged a purified portion of the crude 1-phenylcyclohexyl hydroperoxide prepared in the first stage containing 73% of 1-phenylcyclohexyl hydroperoxide (Run A) and the unpurified first stage crude 1-phenylcyclohexyl hydroperoxide containing 22.8 wt. % hydroperoxide (Run B). Purification of the Run A hydroperoxide reactant was accomplished by first subjecting the crude hydroperoxide to distillation at 50°–90°C., under 0.3 mm. Hg pressure followed by extracting at ambient temperature the residue with 10 ccs pentane per gram of distillation residue to remove the pentane insoluble impurity hydroperoxide. To the flask there were further charged acetone, ortho-dichlorobenzene (internal standard for G. C. analysis) and acetone washed sulfonated polystyrene (Amberlyst 15). The resultant mixture was stirred for two hours at about 25°C. The test data and results are reported below in Table I:

TABLE I

| RUN | A | B |
|---|---|---|
| React. Ingred., g. | | |
| Hydroperoxide Oxidate | 0.68 | 2.5 |
| Acetone | 2.0 | 2.0 |
| o-Dichlorobenzene | 0.25 | 0.26 |
| Amberlyst 15 | 0.25 | 0.25 |
| Purity Hydroperoxide | Purified | Unpurified |
| *Yield, wt. % | | |
| Phenol | 87 | 86 |
| Cyclohexanone | 81 | 67 |

*Yield based on pure hydroperoxide input.

EXAMPLE II

This example illustrates the method of the invention and the desirability of employing cumene and an alkanone and removing excess cumene from the crude 1-phenylcyclohexyl hydroperoxide intermediate product.

Two runs were made. In Runs C and D to a 1-liter glass reactor equipped with a reflux condenser fritted glass sparger and mechanical stirrer, there were charged 320 grams of a mixture of 25 wt. % of cyclohexylbenzene and 75 wt. % of cumene. The reaction ingredients were maintained at 120°C. via an oil bath and oxygen was introduced at a rate of 0.2 liter per minute. After 360 minutes 22.1 mole % of cyclohexylbenzene and 25.9 mole % of cumene had been converted with respective selectivities of 84.2 and 89.7 mole % to 1-phenylcyclohexyl hydroperoxide and cumyl hydroperoxide respectively. In Run C the portion of the crude 1-phenylcyclohexyl hydroperoxide product was purified by removing excess cumene and the purified product was charged to a 0.1 liter flask fitted with a mechanical stirring device and reflux condenser together with acetone, o-dichlorobenzene (internal standard) and sulfonated polystyrene (Amberlyst 15). The reaction was conducted under ambient conditions of temperature (~25°C.) and pressure (~1 atm.). In Run D, Run C was repeated with the exception that cumene was not removed from the intermediate and acetone was not added. The test data and results are reported below in Table II:

TABLE II

| RUN | C | D |
|---|---|---|
| Reactants, g. | | |
| Hydroperoxide Oxidate | 1.16 | 2.50 |
| Amberlyst 15 | 0.25 | 0.25 |
| Acetone | 1.36 | None |
| o-Dichlorobenzene | 0.23 | 0.26 |
| Cumene Removed | 1.36 | None |
| Yield, Wt. % | | |
| Phenol | 99 | 91 |
| Cyclohexanone | 94 | 72 |

EXAMPLE III

This example illustrates the preferred embodiment of the invention and its advantages, namely the use of cumene in the first stage of the reaction.

In the oxidation stage of the reaction, the reaction took place in a 1-liter glass reactor equipped with a reflux condenser fritted glass sparager and mechanical stirring device. The cyclohexylbenzene and cumene were charged to the reactor and the reactor was maintained at 120°C. while oxygen was sparged therethrough at a flow rate of 0.2 liters/minute. In the runs representing the preferred procedure (Runs E, F and G) excess cumene was removed. In the acid cleavage second stage a portion of the first stage product (purified or unpurified) was then introduced into a reactor consisting of 0.1 liter flask fitted with a mechanical stirring device and reflux condenser. All second stage reactions were carried out for two hours under ambient conditions of temperature (~25°C.) and pressure (~1 atm.) utilizing acetone (except Run H) and sulfonated polystyrene (Amberlyst 15) as catalyst which had been acetone washed. The second stage reaction mixture also includes about 0.25 g. ortho-dichlorobenzene as an internal standard for gas chromatography analysis. The test data and results are reported below in Table III:

TABLE III

FIRST STAGE

| RUN | Reaction Mixture Cumene | Wt. % CHB[1] | Reaction Time, Hrs. | Product Yield, Wt.% CHP[2] | CHBHP[3] |
|---|---|---|---|---|---|
| D | — | 100 | 11 | — | 22.8 |
| E | 25 | 75 | 9 | 6 | 13.8 |
| F | 50 | 50 | 7 | 13.1 | 10.8 |
| G | 75 | 25 | 6 | 20.4 | 5.3 |
| H | 100 | — | 4.5 | 29.1 | — |

SECOND STAGE

| RUN | 1st Stg. Ox. Prod., g. | Acetone, g | Acetone | Yield % Theory Cyclohexanone | Phenol |
|---|---|---|---|---|---|
| D | 2.5 | 2 | 82 | 67 | 86 |
| E | 1.99 | 0.54 | 84 | 82 | 90 |
| F | 1.54 | 0.98 | 83 | 84 | 91 |
| G | 1.16 | 1.36 | 99 | 94 | 99 |

TABLE III-continued

| H | 2.5 | — | 96 | — | 96 |

¹CHB = Cyclohexylbenzene
²CHP = Cumene hydroperoxide
³CHBHP = 1-phenylcyclohexyl hydroperoxide

We claim:

1. A method of preparing phenol and cyclohexanone comprising first contacting a mixture of cyclohexylbenzene and a member selected from the group consisting of cumene and cumene hydroperoxide with an oxygen containing gas at a temperature between about 90° and 140°C. in an initial mole ratio of said cyclohexylbenzene to said member of between about 1:99 and 99:1, utilizing a mole ratio of oxygen to said cyclohexylbenzene of at least about 3:1 to form a second mixture of 1-phenylcyclohexyl hydroperoxide and cumyl hydroperoxide, and subsequently removing excess cumene and at least a portion of excess cyclohexylbenzene from said second mixture followed by second contacting said second mixture with an alkanone of from 3 to 6 carbons and an acid cleavage catalyst selected from the group consisting of hydrocarbyl sulfonic acid and mineral acid at a temperature between about 20° and 50°C. and recovering phenol and cyclohexanone from the final product, said catalyst being present in said second contacting in a concentration between about 10 and 30 wt. % based on the reaction mixture and said alkanone being present in said second contacting in a concentration of between about 20 to 80% based on the reaction mixture.

2. A method in accordance with claim 1 wherein said catalyst is sulfonated polystyrene, and said alkanone is acetone.

* * * * *